US008993802B2

(12) United States Patent
Heinz et al.

(10) Patent No.: US 8,993,802 B2
(45) Date of Patent: Mar. 31, 2015

(54) SODIUM DIFORMATE PRODUCTION AND USE

(71) Applicant: BASF SE, Ludwigshafen (DE)

(72) Inventors: Robert Heinz, Ludwigshafen (DE); Otto Machhammer, Mannheim (DE); Stefan Gropp, Ludwigshafen (DE); Alexander Hauk, Ludwigshafen (DE); Gerd Diebold, Reutlingen (DE); Anna Valeska Lohmann, Limburgerhof (DE); Dieter Feuerstein, Dudenhofen (DE); Robert Rühle, Carlsberg (DE); Rüdiger Schmitt, Ludwigshafen (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/922,418

(22) Filed: Jun. 20, 2013

(65) Prior Publication Data

US 2013/0281738 A1 Oct. 24, 2013

Related U.S. Application Data

(60) Division of application No. 13/566,376, filed on Aug. 3, 2012, now Pat. No. 8,497,394, which is a continuation of application No. 11/911,292, filed as application No. PCT/EP2006/003398 on Apr. 12, 2006, now abandoned.

(30) Foreign Application Priority Data

Apr. 13, 2005 (DE) .......................... 10 2005 017 089
Feb. 20, 2006 (EP) ..................................... 06003445

(51) Int. Cl.
| | | |
|---|---|---|
| C07C 51/02 | (2006.01) | |
| C07C 53/06 | (2006.01) | |
| A23K 3/03 | (2006.01) | |
| A23K 1/16 | (2006.01) | |
| A23K 1/18 | (2006.01) | |
| A23K 1/175 | (2006.01) | |
| C05F 11/00 | (2006.01) | |

(52) U.S. Cl.
CPC ................. *C07C 53/06* (2013.01); *C07C 51/02* (2013.01); *A23K 3/03* (2013.01); *A23K 1/1609* (2013.01); *A23K 1/184* (2013.01); *A23V 2002/00* (2013.01); *A23K 1/1751* (2013.01); *A23K 1/1826* (2013.01); *C05F 11/00* (2013.01); *A23K 1/1833* (2013.01)
USPC ............................................................ 562/609

(58) Field of Classification Search
CPC ........... C07C 51/02; C07C 53/06; A23K 3/03
USPC ....................................................... 562/609
See application file for complete search history.

(56) References Cited

U.S. PATENT DOCUMENTS 6,906,222 B2 6/2005 Slany et al.

FOREIGN PATENT DOCUMENTS

| | | |
|---|---|---|
| DE | 424017 A1 | 1/1926 |
| DE | 10231891 A1 | 1/2004 |
| WO | WO-96/35337 A1 | 11/1996 |
| WO | WO 96/35657 | * 11/1996 |
| WO | WO-96/35657 A1 | 11/1996 |
| WO | WO-03/040078 A1 | 5/2003 |
| WO | WO-2004/057977 A1 | 7/2004 |

OTHER PUBLICATIONS

Elöd, E., et al., Anorganische and Allgemeine Chemie, vol. 165, Nr. 1, pp. 161-170; (2014); (ISSN: 0863-1786, DOI: 10.1002/zaac.19271650117) (cited in European parent application EP 067244298.2).

Translation of Elöd, E., et al., "The Ternary System HCOOH—HCOONa-H$_2$0, Information on Acidic Sodium Salts for Formic Acid", (2014).

* cited by examiner

*Primary Examiner* — Yevegeny Valenrod
(74) *Attorney, Agent, or Firm* — Drinker Biddle & Reath LLP (57) ABSTRACT

The invention relates to a method for producing and using a solid sodium diformate having a high formic acid content, to the use thereof in animal foods in the form of an acidifier, preservatives, ensilage auxiliary agents, fertilizers, and a growth and productivity-stimulating agent and the inventive animal food additives containing sodium diformate.

5 Claims, 2 Drawing Sheets

SODIUM DIFORMATE PRODUCTION AND USE

RELATED APPLICATIONS

This application is a divisional application of U.S. patent application Ser. No. 13/566,376, filed Aug. 3, 2012, which is a divisional application of U.S. patent application Ser. No. 11/911,292, filed Oct. 11, 2007, which is a national stage application (under 35 U.S.C. §371) of PCT/EP2006/003398, filed Apr. 12, 2006, which claims benefit of German Application No. 10 2005 017 089.7, filed Apr. 13, 2005, and European Application No. 06003445.1, filed Feb. 20, 2006.

The present invention relates to a method for producing sodium diformate in solid form having a high formic acid content, use thereof in animal feeds, as acidifier, preservative, silage aid, fertilizer and growth and performance promoter, and also to animal feed additives comprising the inventive sodium diformate.

Formic acid formates have antimicrobial activity and are used, for example, for preserving and acidifying plant and animal materials, for instance grasses, agricultural products or meat, for treating biowastes, or as an additive for animal nutrition.

In the animal nutrition sector, as sodium compounds, use is generally made of either mixtures of sodium diformate with trisodium hydrogenformate, or the latter alone, see, e.g., WO 96/35337 and WO 04/57977. WO 96/35337, furthermore, reports on the use of sodium diformate, but no specific instructions on production of this compound are given.

Generally, a content of formate anions as high as possible as one of the active constituents is desirable for the use of hydrogenformates. From the economic aspect, it is advantageous in particular if this increased content of formate anions is accompanied by a formic acid fraction as high as possible, since this simultaneously offers the acidifying activity. Under these aspects, the use of formic formic acid sodium formate is particularly expedient, since, in this case, compared with trisodium hydrogentetraformate, and also compared with formic formic acid potassium formate, in each case a higher theoretical content, both in formate ions and in formic acid is present. Although both values are somewhat more expedient in the case of ammonium diformate, this is, however, a very unstable compound.

Formic acid formates in solid form and their production have long been known as such, e.g. from Gmelins Handbuch der anorganischen Chemie [Gmelin's handbook of inorganic chemistry], 8th edition, number 21, pages 816 to 819, Verlag Chemie GmbH, Berlin 1928 and also number 22, pages 919 to 921, Verlag Chemie GmbH, Berlin 1937. According to these citations, the formic acid formates potassium diformate and sodium diformate are said to be obtainable in principle by dissolving potassium formate or sodium formate in formic acid and subsequently cooling. In addition to sodium diformate, the more stable crystal form trisodium hydrogenformate exits. However, reference is made to the fact that especially sodium diformate is accessible only with difficulty in crystalline dry form and, furthermore, is relatively unstable. The statements in Gmelin's handbook only permit the conclusion that the products described there were not pure sodium diformate.

EP 0 824 511 B1 describes a method for producing products which comprise disalts of formic acid. In this process, certain alkali metal or ammonium formates, hydroxides, (bi) carbonates or ammonia are mixed at 40° C. to 100° C. with formic acid which has a content of at least 50%. The mixture is subsequently cooled and the disalts are obtained by filtration. Although the production of formic acid potassium formate and also of mixtures of formic acid sodium formate with trisodium hydrogentetraformate are presented by way of example, the production of solid pure sodium diformate, in contrast, is not taught. Thus, the temperatures and concentration limits specified for the method for the (aqueous) potassium and sodium formate solutions to be used in the method only permit the production of potassium diformate, since (aqueous) solutions of sodium formate cannot be produced in the concentrations specified, owing to the lower solubility limit compared with potassium formate. Therefore, although potassium diformate is obtained, sodium diformate is present solely in a mixture with trisodium hydrogentetraformate.

German patent DE 42 40 17 (of 14.01.1926) teaches the production of formic acid sodium formates having various acid contents by introducing sodium formate into aqueous formic acid. The resultant crystals are obtained by cooling the solution to ambient temperature. Depending on the water content of the formic acid, in addition to trisodium hydrogenformate and mixtures of trisodium hydrogenformate with sodium diformate, sodium diformate is also said to be accessible. The latter is said to be obtained by the method of DE 424017 when the formic acid used has a content of more than 50%, e.g. 80%, as in example 2. The inventors' own experiments, however, found that, under the conditions specified in DE 424017, sodium diformate cannot be obtained in pure, crystalline form. Rather, in this procedure a mixture with trisodium hydrogenformate is obtained, the formic acid content of which is markedly below the expected theoretical value for pure sodium diformate of 40.36% by weight, based on the total dry weight.

Consequently, it has not been possible to date to produce solid sodium diformate having a formic acid content of at least 35% by weight in pure, stable and dry form.

Adequate stability of formic acid sodium formate in solid form is of particular importance not only with respect to handling and storage life, but also with respect to production. In particular, release to any great extent of the formic acid present in the formic acid sodium formate is undesirable owing to Its corrosive activity.

In the animal nutrition sector, sodium diformate offers the advantage that the trace element sodium need not be added separately in the form of NaCl, as is otherwise customary, but already represents a sodium source as such. Owing to the high formic acid content in sodium diformate, e.g. compared with trisodium hydrogentetraformate, the content of sodium ions is limited. A low or limited content of cations, e.g. including potassium ions, is desirable inasmuch as the latter, in particular in the case of monogastric animals and especially in the case of poultry can lead to an increased liquid intake (increased drinking) and thus to dilution of the excreta of the animals, that is to say can develop diuretic activity.

The object underlying the present invention was to provide a method for producing sodium diformate in solid form and of high purity, i.e. especially having a high formic acid content. The inventive method should, in particular, enable the production of a sodium diformate in comparatively stable and dry form and thus open up a route to its industrial production.

This object has surprisingly been achieved by crystallizing out the target compound from a mixture of sodium formate with a more than one and a half times molar excess of concentrated or aqueous formic acid while maintaining a molar ratio of formic acid to water of at least 1.1:1.

The present invention therefore firstly relates to a method for producing sodium diformate in solid form having a formic acid content of at least 35% by weight, based on the total weight of sodium diformate, which comprises producing, at elevated temperature, from sodium formate and aqueous or concentrated formic acid having a formic acid content of at least 74% by weight, a homogeneous mixture which has a molar ratio of HCOOH to Na[HCOO] of greater than 1.5:1 and a molar ratio of formic acid to water of at least 1.1:1, cooling the mixture and separating off the solid phase from the mother liquor.

The method according to the invention makes possible for the first time the production of a sodium diformate in solid dry form having a formic acid content of at least 35% by weight, frequently at least 36% by weight, in particular at least 37% by weight, especially at least 38% by weight, very especially at least 39% by weight, and still more especially at least 40% by weight, in each case based on the total weight of the sodium diformate. A sodium diformate of this type is therefore a further subject matter of the invention.

A homogeneous mixture in the meaning of the present invention is taken to mean a clear aqueous solution of formic acid in which all of the sodium formate present in the solution is in dissolved form. If appropriate this inventively produced homogeneous mixture comprises sodium diformate crystals for the purpose of seeding the crystallization, as described hereinafter in detail. To this extent, the term "homogeneous mixture" used here comprises not only the aqueous solution comprising formic acid and dissolved sodium formate, but also the sodium diformate crystals which are added if appropriate.

The starting materials sodium formate and formic acid used in the present invention are commercially available and can be used as such without pretreatment.

The sodium formate present as solid at room temperature can be used, e.g., as technical-grade sodium formate. Sodium formate occurring in the production of polyols as waste product is also suitable for use in the present invention. Generally, use is made of a sodium formate whose Na[HCOO] content is at least 97% by weight, based on the total weight of the sodium formate source used. Preferably, use is made of a sodium formate which comprises less than 0.1% by weight, and in particular less than 0.05% by weight, potassium ions, in each case based on the total weight of the sodium formate source used.

It is likewise possible to produce in situ the sodium formate intended for the reaction with formic acid, e.g. by reacting sodium hydroxide, carbonate or hydrogencarbonate with formic acid in concentrated aqueous solution, by reacting carbon monoxide with liquid sodium hydroxide, or by reacting methyl formate with sodium hydroxide. In the case of this variant, a procedure can be followed, e.g., such that solid NaOH or a concentrated aqueous solution thereof, if appropriate with cooling and/or stirring, is dissolved in concentrated formic acid. The ratios of the starting materials can advantageously be directly chosen such that the components formic acid, sodium formate and water in the resultant mixture are already in the abovementioned molar ratios which are required. Otherwise, generally neutralization of excess formic acid and/or a reduction of the water content of the mixture by conventional methods known to those skilled in the art, e.g. evaporation, extraction, distillation and the like, are necessary. Moreover, in this variant the statements made for the general process procedure can be followed.

According to the invention use is made of an aqueous formic acid solution having a formic acid content of at least 74% by weight, or a concentrated formic acid. The concentrated formic acid is taken to mean by those skilled in the art a formic acid solution having a formic acid content of 94% by weight or more, i.e. having a residual water content of less than 6% by weight, in each case based on the total weight of formic acid solution. As aqueous formic acid, a solution of formic acid in water having a formic acid content of less than 94% by weight, based on the total weight of the aqueous formic acid solution. The aqueous formic acid solution used preferably has a concentration of at least 75% by weight, preferably at least 80% by weight, and particularly preferably at least 90% by weight. Very particularly preferably, use is made of concentrated formic acid having a formic acid content of at least 94% by weight. The concentration of the formic acid or solution will preferably not exceed 99% by weight, and is particularly preferably in the range from 80 to 99% by weight, and especially in the range from 94 to 98% by weight.

Preferably, use is made of concentrated or aqueous formic acid in an amount of at least 1.6 mol, in particular at least 1.8 mol, and especially at least 2.0 mol of HCOOH per mol of Na[HCOO]. Preferably, the molar ratio used of HCOOH:Na[HCOO] will lie in the range from 1.6:1 to 3:1, and in particular in the range from 1.8:1 to 2.5:1.

In addition, use will preferably be made of the respective starting materials in amounts such that the molar ratio of $HCOOH:H_2O$ in the homogeneous mixture is at least 1.5:1, and particularly preferably at least 1.8:1; very particularly preferably, it is in the range 1.5:1 to 10:1, and in particular in the range from 1.8:1 to 6.1:1, The sequence in which the starting materials are used is of subsidiary importance. Advantageously, the mixture proceeds in such a manner that a homogeneous liquid mixture of the starting materials is obtained in the molar ratio which is to be kept. According to the invention, the homogeneous mixture is produced at elevated temperature. This is generally taken to mean temperatures of at least 30° C., in particular at least 40° C., and especially at least 50° C. Said homogeneous mixture can be produced using conventional procedures known to those skilled in the art, e.g. by mixing, stirring and/or dissolving, using elevated temperature, or by a combined use of these methods.

To carry out the inventive method, generally a procedure is followed such that an aqueous or concentrated, preferably concentrated, solution of formic acid is initially charged. To this formic acid solution is added the sodium formate in solid form, or in the form of an aqueous solution or suspension. The addition can proceed in portions, e.g. in 2, 3, 4 or more individual portions which are added to the mixture at a predetermined time interval from one another, or continuously, i.e. at constant, decreasing, or increasing, rate. During the addition, generally a temperature increase occurs, so that if appropriate additional heating is not necessary. Customarily, the temperature of the mixture is set, e.g. by matching the addition rate and/or cooling or heating of the mixture and/or of the solution or suspension added, in such a manner that in the mixture a temperature in the range from 30° C. to 80° C., and in particular from 40° C. to 70° C., is maintained. Preferably, the temperature of the mixture is not above 65° C. It is essential to the invention that the crystallization proceeds from an aqueous solution. This solution, as set forth below, can be admixed, or become admixed, with seed crystals as soon as before the start of crystallization.

During the addition of sodium formate, the solution or suspension is advantageously agitated, e.g. stirred. The agitation is continued until termination of the addition, at least until a homogeneous mixture is obtained, generally until the end or termination of the crystallization.

According to the invention the starting materials can be mixed in all reactors, kettles, flasks, containers and other apparatuses, in particular in stirred tanks having internal heat exchange surfaces, customarily used for producing a homogeneous liquid mixture. These are known to those skilled in the art. To avoid corrosion effects, e.g. in the case of reactors or kettles made of steel, it is advantageous if the surfaces and walls coming into contact with formic acid are coated with an acid-resistant protective layer, e.g. of Teflon®, or are lined with especially acid-resistant high-alloy steels.

Subsequently, the mixture, preferably with continued stirring, is brought to crystallization. This can be achieved, e.g., by partial evaporation or cooling, preferably by cooling. If the crystallization is caused, or initiated or accelerated by a controlled evaporation of the liquid phase, preferably under vacuum, it will generally be ensured that the molar ratios of the components in the homogeneous mixture are within the above specified ranges at the start of, and during, the crystallization. If appropriate, in this case, however, the ratio of HCOOH to $H_2O$ can shift toward higher molar ratios than in the starting solution in the course of crystallization. If the crystallization is effected by cooling, this is preferably performed slowly, advantageously over a time period of one to a plurality of hours, e.g. up to 24, or up to 12 h, in particular from 1 to 15 h, especially from 2 to 10 h, more especially from 3 to 10 h and very especially from 4 to 8 h. In this case the sodium diformate crystallizes out. It has proved to be advantageous if the cooling proceeds at a cooling rate in the range of about 1 to about 30 K/h, and in particular of about 2 to about 20 K/h, e.g. about 5 to 15 K/h. To achieve a substantial crystallization of the target compound, it is advantageous to cool the reaction mixture within the said period to a temperature of below 30° C., e.g. about 25, 20, 15 or 10° C. or below, in particular below 20° C., e.g. about 18° C. or below, or 16° C. or below. Generally, in this case, the temperature will not fall below 0° C., in particular 5° C., especially 10° C., and very especially 15° C.

It has proved to be advantageous, after the initiation of crystal formation, to dissolve the crystal seeds or small crystals first formed by heating, e.g. to a temperature of at most 65° C., in particular in the range from 25° C. to 50° C., and then to reinitiate the crystallization process by renewed, if appropriate retarded, cooling. During this renewed cooling, the rate is customarily in the range from about 0.5 to about 20 K/h, e.g. from about 1 to 15 K/h, in particular about 2 to 15 K/h, especially about 5 to 10 K/h, and preferably at at most 25 K/h. The crystallization temperature is in the abovementioned ranges.

In addition, it can be advantageous to add to the mixture preexisting crystals of sodium diformate, e.g. crystals produced in advance by the inventive method, to promote the crystallization operation, i.e. for the purpose of what is termed "seeding". Such crystals can be added in dry or moist form, suspended in a liquid phase, e.g. aqueous or formic acid phase, or a combination of these forms. In this case the addition generally proceeds above a temperature which leads to a crystal formation, but below a temperature at which a homogeneous solution is present. The temperature of the reaction mixture therefore generally not exceeds 65° C. during the addition of crystals, and will preferably be in the range from 25 to 50° C. The crystallization operation can then proceed as described above, at a cooling rate in the range from about 0.5 to about 20 K/h, e.g. about 1 to 15 K/h, in particular about 2 to 15 K/h, and especially about 5 to 10 K/h. The crystallization temperature is in the abovementioned ranges.

Subsequently to the crystallization, the resultant solid product is separated off from the mother liquor. The solid phase can be separated off from the mother liquor by methods which are customary for this and are known to those skilled in the art, e.g. filtration or centrifugation, preferably by centrifugation, in particular by using pusher-type or peeler centrifuges. In the course of this separation, the mother liquor is frequently removed to the extent that the solid phase which is separated off has a water content in the range from 2 to 0.2% by weight, in particular in the range from 1.5 to 0.4% by weight, and especially in the range from 1 to 0.5% by weight, in each case based on the total weight of the solid phase which is separated off. Moreover, the mother liquor is frequently removed to the extent that the solid phase which is separated off has a formic acid content in the range from 40.5 to 43.5% by weight, in particular in the range from 41 to 43% by weight, especially in the range from 41 to 42.5% by weight, and very especially in the range from 41 to 42.2% by weight, in each case based on the total weight of the solid phase which is separated off.

Customarily, the moist product thus obtained is subsequently dried by drying methods, e.g. under vacuum and/or moderate heating. Dryers and drying methods which are usable for this are known per se to those skilled in the art and are described, e.g. in K. Kröll, Trockner and Trocknungsverfahren [Dryers and drying methods], 2nd edition, Springer Verlag, Berlin 1978, However, in this case, the relatively high volatility of the formic acid present in the product and also the limited temperature stability of the product must be taken into account. It is therefore generally necessary to control the drying conditions within relatively narrow parameter ranges, as set forth in detail hereinafter.

Alternatively, or supplementary, the moist product or the dry material can be admixed or mixed with desiccants known to those skilled in the art. This is a customary procedure in order to improve in particular the flowability of the resultant product. Suitable materials for this are, e.g., desiccants such as silicic acid, e.g. the Sipernat brands from Degussa, inorganic alkali metal salts and alkaline earth metal salts, e.g. Mg, Ca, Zn, Na, K sulfates, carbonates, silicates or phosphates; in addition inorganic buffers such as alkali metal hydrogenphosphates, in particular sodium and potassium hydrogenphosphates, e.g. $K_2HPO_4$, $KH_2PO_4$ and $Na_2HPO_4$.

During the drying, the product is advantageously agitated in the dryer. This can proceed, in particular, via mechanical elements, e.g. mixer blades, or via a gag stream, e.g. a customary fluidized bed. Particularly suitable drying apparatuses or dryers are, e.g., contact dryers, fluidized-bed dryers and jet dryers, if appropriate spray dryers can be used. Those which are especially suitable are blade dryers, and in the case of drying under reduced pressure, especially vacuum blade dryers, or convective dryers equipped with mixer blades, e.g. from Forberg.

Preferably, the solid phase which is separated off from the mother liquor will be dried at a product temperature of no more than 60° C., in particular no more than 55° C., and especially no more than 50° C.

Preferably, the solid phase which is separated off from the mother liquor will be dried at a pressure of at most $10^5$ Pa. In the case of drying under reduced pressure, this is preferably at most $10^4$ Pa, and particularly preferably at most $6·10^3$ Pa, e.g. in the range from $1·10^3$ Pa to $6·10^3$ Pa. Particularly advantageous results are achieved by vacuum drying at a pressure of less than $4·10^3$ Pa, e.g. in the range from $1·10^3$ Pa to $3.5·10^3$ Pa.

In a preferred embodiment, drying proceeds by means of contact drying at a wall temperature of at most 100° C., particularly preferably at most 80° C., and very particularly preferably at most 65° C. In this case the vapors can be removed by a stripping gas stream, e.g. air or nitrogen. When such a stripping gas stream is used, customarily such an amount of gas is allowed to flow through the drying apparatus per hour that approximately corresponds to the order of magnitude of the volume of the respective drying apparatus. Particularly preferably, the contact drying is carried out at a pressure in the range from $2 \cdot 10^3$ Pa to about atmospheric pressure, e.g. in the range from $2 \cdot 10^3$ Pa to $1 \cdot 10^4$ Pa.

In a further preferred embodiment, drying proceeds by means of convective drying at a carrier gas inlet temperature in the range from 20 to 120° C., more preferably in the range from 50 to 100° C., particularly preferably in the range from 60 to 90° C. A suitable carrier gas is, e.g. air or nitrogen. The carrier gas stream can be conducted in a known manner linearly or in a circle through the drying apparatus. If appropriate, the carrier gas is subjected before the drying operation to conditioning (predrying); obviously, such an operation can also be connected downstream of the drying operation, so that the gas dried in such a manner, e.g. by means of condensation or adsorption, can be reused as carrier gas for the product drying. Customarily, an amount of gas is allowed to flow through the drying apparatus per hour such that this approximately corresponds to 100 times to 10 000 times the volume of the respective drying apparatus.

The water content remaining in the product after drying (residual water content) is generally no more than 0.5% by weight, and is customarily in the range from about 0.5 to 0.01% by weight, preferably at most 0.3% by weight, more preferably at most 0.2% by weight, particularly preferably at most 0.15% by weight, and very particularly preferably at most 0.1% by weight, based on the total weight, determined by oxidimetric titration according to Karl Fischer (e.g. described in Wiland, Wasserbestimmung durch Karl-Fischer-Titration [Water determination by Karl-Fischer titration], Darmstadt, GIT, 1985).

The inventive method can be carried out continuously, batchwise or semibatchwise. In this case the sodium diformate is obtained in solid dry form as described, with the mother liquor completely or in part advantageously being able to be reused for producing the starting mixture, or for adjusting the molar concentration ratios in the starting material stream. The mother liquor, after separating off the crystals, can be neutralized, e.g. using sodium hydroxide solution, essentially a sodium formate solution resulting which if appropriate can be evaporated or again brought to crystallization.

The sodium diformate in solid dry form is obtained by the inventive method in high purity and therefore has a high formic acid content, generally at least 35% by weight, frequently at least 36% by weight, In particular at least 37% by weight, especially at least 38% by weight, very especially at least 39% by weight, and still more especially at least 40% by weight, in each case based on the total weight of the sodium diformate. Generally, the formic acid content in the inventive sodium diformate will be no more than 41% by weight, and in particular no more than 40.5% by weight, in each case based on the total weight. Especially, the content is in the range from 38 to 41% by weight, more especially in the range from 39 to 41% by weight, and very especially in the range from 39 to 40.5% by weight, or in the range from 40 to 41% by weight, in each case based on the total weight of the sodium diformate obtainable.

Here and hereinafter, the expression total weight of sodium diformate is used synonymously with the expression total dry weight. The total dry weight is to be taken to mean the weight of sodium diformate which is given by drying the product below its decomposition temperature, e.g. by drying over a period of 1 h at a temperature of 35° C. and at a pressure of 50 mbar. The formic acid content in the dry product can be determined in a conventional manner, e.g. by titration of the formic acid with a base. Clearly, a high content of formate anions is likewise present in the dry product.

The inventively produced sodium diformate is typically obtained in crystalline form. It is assumed that it essentially or completely corresponds to the formula Na[HCOO].HCOOH, but which is not to be taken to mean a limit of the invention. At about 65° C., a phase transition point may be observed by means of DSC (differential scanning calorimetry). The inventively obtained crystalline modification of sodium diformate may be identified, for example, via x-ray wide angle scattering. Unwanted modifications, e.g. trisodium hydrogentetraformate, can likewise be detected qualitatively by the same method. The statement of the x-ray diffraction reflections is made in the present application in the form of the lattice separations d [Å] which are independent of the wavelength of the x-ray radiation used, which separations may be calculated from the measured diffraction angle using the Bragg formula.

Generally, the x-ray powder diffractogram of the inventive sodium diformate exhibits all diffraction reflections characteristic of the specific crystal structure. Depending on the degree of crystallinity and the texturing of the resultant crystals, however, a decrease in the intensity of the diffraction reflections can occur in the x-ray powder diffractogram, which can be to such an extent that individual lesser-intensity diffraction reflections are no longer detectable in the x-ray powder diffractogram. Individual lesser-intensity diffraction reflections can therefore be absent or the intensity ratio can be modified in the x-ray powder diffractogram. The presence of all of the respectively stated diffraction reflections in the x-ray powder diffractogram is an indication that compounds of particularly high crystallinity are involved. It is obvious to those skilled in the art that the inventive sodium diformate, in addition to the respectively stated characteristic diffraction reflections, can have further diffraction reflections. In addition, mixtures of the inventive sodium diformate with other crystalline compounds generally have additional diffraction reflections.

The x-ray powder diffractogram of the inventive sodium diformate is customarily characterized by diffraction reflections at at least 6, in particular at least 8, and especially at least 10, lattice separations selected among d=8.99; 7.40; 6.69; 5.12; 4.37; 3.83; 3.40; 3.10; 2.98; 2.94; 2.90 [Å] (±0.04 [Å]). Further diffraction reflections are frequently observed at the following lattice separations: d=8.01; 4.89; 3.97; 3.50; 3.35; 3.25; 3.02; 2.83; 2.69; 2.44; 2.22 and/or 2.16 [Å] (±0.04 [Å]). It is obvious to those skilled in the art that very closely adjacent lattice separations can be superimposed over one another in the x-ray powder diffractogram. Typical relative intensities obtained in the x-ray powder diffractogram are listed in table 1.

TABLE 1

| Diffraction reflections | d (±0.04) [Å] | $I_{ref}$ [%] |
|---|---|---|
| 1 | 8.99 | 100 |
| 2 | 8.01 | 14.4 |
| 3 | 7.40 | 23.2 |
| 4 | 6.69 | 91.4 |
| 5 | 5.12 | 26.2 |
| 6 | 4.89 | 17.5 |
| 7 | 4.37 | 21.6 |
| 8 | 3.97 | 11.7 |
| 9 | 3.83 | 43.6 |
| 10 | 3.50 | 18.3 |
| 11 | 3.40 | 29 |
| 12 | 3.35 | 16 |
| 13 | 3.25 | 19.9 |
| 14 | 3.10 | 39.1 |
| 15 | 3.02 | 19.9 |
| 16 | 2.98 | 49.7 |
| 17 | 2.94 | 48 |
| 18 | 2.90 | 31.5 |
| 19 | 2.83 | 18.8 |
| 20 | 2.69 | 16.7 |
| 21 | 2.44 | 16.7 |
| 22 | 2.20 | 16 |
| 23 | 2.16 | 16.7 |

The sodium diformate produced according to the invention is generally obtained in a purity such that the molar ratio of the components sodium formate and formic acid is customarily in the range from 0.9:1 to 1.1:1; in particular in the range from 0.95:1 to 1.05:1, and especially corresponds to about 1:1. The fraction of sodium diformate in the solid product obtained is customarily at least 97% by weight, in particular at least 98% by weight, and especially at least 99% by weight, in each case based on the total weight of solid product. As further constituents, the product may comprise, owing to residual moisture or crystallized residual moisture, generally up to 1.5% by weight of formic acid, up to 1.5% by weight of sodium formate and/or up to 0.5% by weight of water, in each case based on the total weight of the product.

The sodium diformate produced according to the invention is distinguished by a relatively low hygroscopicity, in particular compared with trisodium hydrogentetraformate. Furthermore, the sodium diformate obtained according to the invention is sufficiently stable to ensure problem-free handling and (further) processing. In addition, the potassium ion content of the inventive sodium diformate is generally at most 1000 ppm, and in particular at most 500 ppm, in each case based on the total weight. Owing to production conditions, the chloride content in the inventive sodium diformate is generally less than 1500 ppm, and in particular less than 1000 ppm, in each case based on the total weight.

The inventive method for producing solid, dry sodium diformate in crystalline, pure and stable form makes it possible for the first time to apply the production conditions to an industrial scale.

Depending on the desired application, the inventively produced sodium diformate can be further processed, in particular powders of defined particle sizes can be produced, the particles produced can be coated with coating materials and/or mixtures with other additives can be produced. As examples of coating materials, oils such as soybean oil, fats and fatty acids such as palmitic or stearic acid or polymer coatings, e.g. of polyalkylenes and derivatives thereof may be mentioned. Customary additives are, in particular, anticaking aids and desiccants such as those mentioned above, e.g. silicic acid etc. Customary methods for coating and also the additives coming into consideration are thoroughly known to those skilled in the art in the respective sector, see, e.g., DE 102 31 891 A1.

The resultant solid product can be comminuted before and/or after the drying step, e.g. by means of mortars, cutters, punch presses and roller mills, agglomerated, e.g. by means of mixers, and/or compacted, e.g. by means of presses and compactors. The apparatuses used for such a commination are known to those skilled in the art.

In a preferred embodiment, the inventive sodium diformate is present in solid form as crystal powder or as granules or compactate. Depending on the application-oriented requirements, the powders, granules or compactates have a mean particle size in the range from 1 µm to 10 000 µm, in particular from 10 µm to 5000 µm, and especially from 100 µm to 2500 µm.

The inventive sodium diformate in solid form and preparations comprising this are suitable for use in feeds for animals (animal feeds), in particular as additive to animal feed in the form of feed additives and especially as additive to premixes for animal feeds. Premixes are mixtures which generally comprise minerals, vitamins, amino acids, trace elements and also, if appropriate, enzymes. Animal feeds and feed additives which comprise the inventive sodium diformate are particularly suitable for monogastric animals such as hogs, especially piglets, breeding sows and fattening hogs, and also poultry, especially broilers, laying hens, turkeys, ducks, geese, quails, pheasants and ostriches.

Depending on the remaining substances or additives present in the feed or feed additive, the content of the inventively prepared sodium diformate in the feed or feed additive can vary greatly. In the case of feed additives, the content furthermore depends on the type of the formulation, e.g. on the addition of aids such as desiccants, on a possible coating and on the residual moisture content. Customarily, the content of inventive sodium diformate in the feed additive is, e.g., in the range from 0.1 to 99.5% by weight, in particular from 0.5 to 75% by weight, and especially from 1 to 50% by weight, based on the total dry weight of feed additive, The inventive sodium diformate is also suitable for use in a premix and can in this case be used, e.g. admixed, in the customary amounts.

In particular, when used in animal feed and feed additives for poultry, a small content of potassium ions is advantageous, since potassium can in this case give rise to a diuretic action. The use of the inventive sodium diformate for the abovementioned purpose thus provides an acidic sodium and formate source, without the fraction of potassium ions being necessarily increased. A further subject of the invention is therefore a solid feed additive which comprises the inventive sodium diformate in solid form and is essentially free from potassium ions. In this case, essentially free from potassium ions means that the content of potassium ions is at most 1000 ppm, and in particular at most 500 ppm, in each case based on the weight of the feed additive.

Animal feeds are composed in such a way that the corresponding nutrient requirement for each animal species is optimally covered. Generally, plant feed components such as corn, wheat or barley meal, whole soybean meal, soybean extraction meal, linseed extraction meal, rapeseed extraction meal, green meal or pea meal are selected as crude protein sources. To ensure an appropriate energy content of the feed, soybean oil or other animal or vegetable fats are added. Since the plant protein sources comprise some essential amino acids only in an insufficient amount, feeds are frequently enriched with amino acids. These are primarily lysine and methionine. To ensure the mineral and vitamin supply of the farm animals, in addition minerals and vitamins are added. The type and amount of added minerals and vitamins depends on the animal species and is known to those skilled in the art (see, for example, Jeroch et al., Ernährung landwirtschaftlicher Nutztiere [Nutrition of agricultural farm animals], Ulmer. UTB). To cover the nutrient and energy requirement, use can be made of complete feeds which comprise all nutrients in a ratio to one another covering requirements. It can form the sole feed of the animals. Alternatively, a supplementary feed can be added to a grain feed of cereals. The supplementary feed can comprise protein-, mineral- and vitamin-rich feed mixtures which supplement the feed.

The inventive sodium diformate is particularly suitable as what is termed an acidifier. Acidifiers are taken to mean those substances which lower the pH. The expression comprises not only those substances which lower the pH in the substrate (e.g. animal feed) but also those which lower the pH in the gastrointestinal tract of the animal, The inventive sodium diformate is suitable, in particular, as a composition having performance- and/or growth-promoting effect. In a preferred embodiment, the solid sodium diformate is used as such a performance- and/or growth-promoting composition for monogastric animals, in particular for hogs and/or poultry.

The inventive sodium diformate is suitable, in addition, as preservative, in particular as preservative for green feeds and/or animal feeds.

The inventive sodium diformate is suitable, in addition, as aid for pharmaceutical preparations, e.g. as disintegrant.

The inventive sodium diformate can advantageously be used in the production of silage. It accelerates lactic acid fermentation or prevents secondary fermentation and inhibits the development of harmful yeasts. In this case it also acts in the manner described above for use as an acidifier, in a regulatory manner on the pH. The invention therefore further relates to the use of the inventive sodium diformate as silage additive (silage aid).

The present invention further relates to the use of the inventive sodium diformate as fertilizer.

DESCRIPTION OF THE FIGURES

FIG. 2 shows, for comparison, a light micrograph of crystallized sodium tetraformate. Significant differences from the sodium diformate crystals may be seen; in particular, the sodium tetraformate is distinguished by a pronounced needle-shaped crystal growth which does not have a correspondence in sodium diformate. On account of the relatively large ratio of length to diameter, the sodium tetraformate needles only achieve in the longitudinal direction the dimensions of the sodium diformate crystals of a few hundred up to over 2000 μm, whereas the needles having a diameter of significantly less than 50 μm do not approximately reach the dimensions of the sodium diformate crystals.

Figure 1:
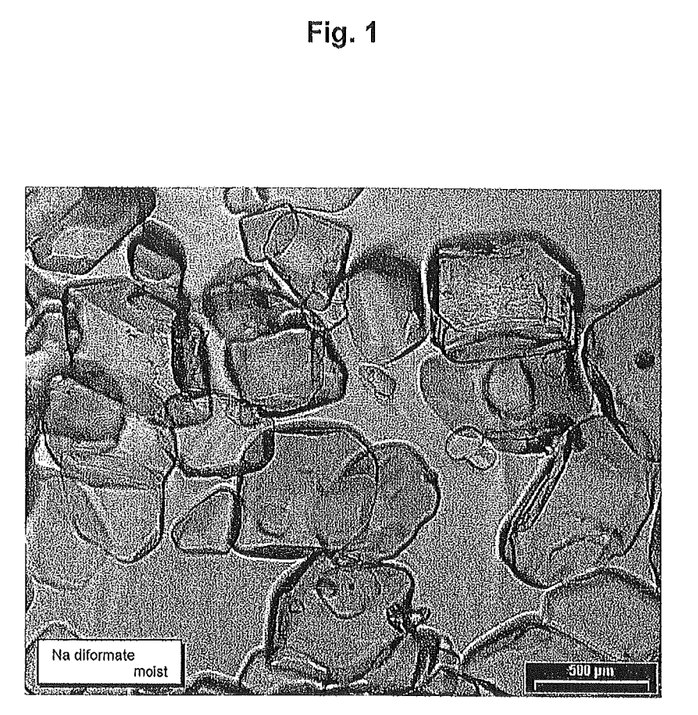
FIG. 1 shows a light micrograph of sodium diformate crystals obtained according to the invention. The size ratios and also an essentially generally hexagonal base shape may easily be recognized.
Figure 2:
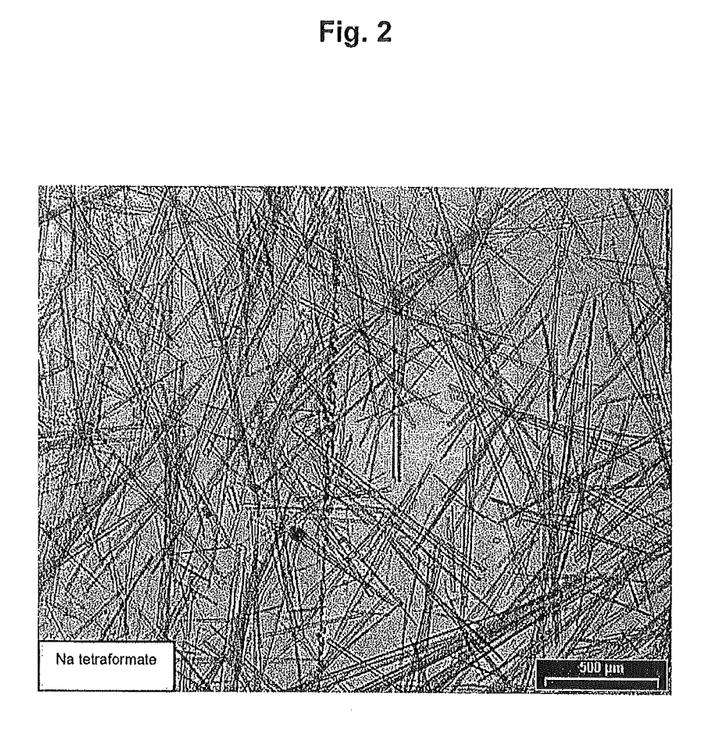

The examples hereinafter serve to illustrate the invention and are in no case to be understood as restricting.

EXAMPLES

Comparative Example

Similar to Example 2 of DE 424017

476 g of an 80% strength by weight aqueous formic acid solution were initially charged. 524 g of solid sodium formate were added with stirring. The mixture was heated to a temperature of 120° C. for complete dissolution. Subsequently, the solution was slowly cooled. Crystallization began from about 112° C. Cooling was further performed to about 25° C. at a rate of about 0.7 K/min. The suspension was then allowed to stand for 24 h with gentle stirring. Thereafter, the crystals formed were separated off from the mother liquor. The yield of moist product was about 370 g. The formic acid content was about 21.8% by weight, based on the total weight of moist product.

Examples 1 and 2

Examples 1 and 2 were carried out in a 1 l stirred vessel which was equipped with heating and cooling apparatus and also an outlet.

Example 1

650 g of a 94% strength by weight aqueous formic acid solution were initially charged and heated to 55° C. with stirring. The stirring was continued for the entire experimental period. 350 g of solid sodium formate (purity>97%) were dissolved in the formic acid solution, a clear solution being obtained. Subsequently, the solution was slowly cooled. After about 4 hours, a temperature of about 12° C. was reached, at which a sudden precipitation was observed. The suspension was heated to about 35° C. until only slight turbidity was still observed. The suspension was then cooled to 20° C. over a period of about 6 h and drained from the stirred vessel. The mother liquor was separated off from the crystals by means of a vacuum filter. The yield of moist sodium diformate was about 125 g. After drying in the vacuum drying cabinet at a temperature of 35° C., the remaining water content in the product was determined at approximately 0.1% by weight, based on the total dry weight of about 122 g. The formic add content in the dry product was 40.3% by weight, based on the total dry weight.

Example 2

650 g of an 80% strength by weight aqueous formic acid solution were initially charged and heated to 55° C. with stirring. Under continued stirring, 430 g of solid sodium formate (purity >97%) were dissolved in the formic acid solution, a clear solution being obtained. Subsequently, the solution was slowly cooled. After about 5 hours, a temperature of about 24° C. was reached, at which a sudden precipitation was observed. The suspension was heated to about 35° C. with stirring, until only a slight turbidity was still observed. The suspension was then cooled to 15° C. over a period of about 6 h with stirring, and drained from the stirred vessel. The mother liquor was separated off from the crystals by means of a vacuum filter. The yield of moist sodium diformate was about 280 g. After drying in the vacuum drying cabinet at a temperature of 35° C., the remaining water content in the product was determined as approximately 0.15% by weight, based on the total dry weight of 270 g. The formic acid content in the dry product was 40.1% by weight, based on the total dry weight.

Examples 3 to 16

Including Vacuum Drying

Example 3

In a vacuum paddle dryer having 5 l usable volume (d=134 mm, l=413 mm, heating surface area=0.156 m$^2$), an amount of product of 2 kg of moist crystals obtained in a similar manner to example 1 or 2 was dried. The residual moisture before the start of drying was 0.6% by weight of water, the formic acid content was about 41% by weight. In the dryer, a wall temperature of 50° C. was set, an absolute pressure of 30 mbar (3000 Pa), a stripping gas stream of 5 l (S.T.P.)/h of nitrogen and a speed of rotation of 10 rpm. In the course of a period of less than 1 h, a residual water content of less than 0.1% by weight was achieved. The formic acid content was about 40.2% by weight. The resultant dry crystals were very free-flowing.

Examples 4 to 16

Examples 4 to 16 were carried out in a similar manner to example 3. in each case a speed of rotation of 10 rpm was employed, in examples 14 and 16 a speed of rotation of 20 rpm. The amount of nitrogen stripping gas stream was in each case 5 l/h, except in example 15, 10 l/h. Further parameter values set as exceptions are indicated in each case in table 2 below. Table 2 also summarizes the results achieved in drying.

TABLE 2

| | Ex. No. | | | | | | | | | | | | |
|---|---|---|---|---|---|---|---|---|---|---|---|---|---|
| | 4 | 5 | 6 | 7 | 8 | 9 | 10 | 11 | 12 | 13 | 14 | 15 | 16 |
| $T_{Wall}$ [°C.] | 22 | 23 | 24 | 24 | 25 | 23 | 40 | 23 | 50 | 60 | 50 | 50 | 50 |
| $T_{Prod}$ [°C.] | 19 | 19 | 21 | 20 | 23 | 22 | 37 | 22 | 47 | 55 | 47 | 47 | 47 |
| $p_{abs}$ [Pa] | 2900 | 3300 | 2700 | 2900 | 5500 | 4400 | 4500 | 5500 | 3000 | 5000 | 3000 | 3000 | 3000 |
| t [min] | 35 | 25 | 25 | 25 | 35 | 104 | 40 | 75 | 35 | 60 | 75 | 55 | 65 |
| $m_{Dry}$ [kg] | 1.91 | 1.93 | 1.90 | 1.88 | 1.43 | 2.22 | 2.28 | 2.09 | 2.01 | 2.25 | 2.25 | 2.25 | 2.25 |
| $H_2O_{Start}$ [% by weight] | 0.66 | 0.66 | 0.65 | 0.65 | 0.65 | 0.58 | 0.58 | 0.56 | 0.56 | 0.96 | 0.96 | 0.76 | 0.76 |
| $H_2O_{End}$ [% by weight] | 0.05 | 0.06 | 0.08 | 0.07 | 0.08 | 0.12 | 0.12 | 0.12 | 0.08 | 0.09 | 0.08 | 0.10 | 0.10 |
| $FA_{Start}$ [% by weight] | 41.26 | 41.26 | 41.48 | 41.48 | 41.48 | 41.17 | 41.17 | 41.28 | 41.28 | 41.66 | 41.66 | 41.42 | 41.42 |
| $FA_{End}$ [% by weight] | 40.63 | 40.79 | 40.80 | 40.75 | 40.68 | 40.80 | 40.75 | 40.75 | 40.56 | 40.21 | 40.59 | 40.46 | 40.79 |

$T_{Wall}$ = temperature of the dryer wall
$T_{Prod}$ = product temperature
$p_{abs}$ = absolute pressure in the dryer
t = total drying time
$m_{dry}$ = total dry weight of the resultant product
$H_2O_{Start}$ = water content in the moist product at the start of drying
$H_2O_{End}$ = water content in the product at the end of drying
$FA_{Start}$ = formic acid content in the moist product at the start of drying
$FA_{End}$ = formic acid content in the product at the end of drying Example 17 to 21

Including Convective Drying

Example 17

In a solids mixture with gas through-flow equipped with cup paddle and having 6 l of usable volume (d=210 mm, l=180 mm), an amount of product of 2 kg of moist crystals obtained in a similar manner to example 1 or 2 was dried. The residual moisture before the start of drying was 0.6% by weight of water, the formic acid content was about 41% by weight. In the dryer, a as stream of 5 m³ (S.T.P.)/h of air or nitrogen at a gas inlet temperature of 50° C. and a mixer speed of rotation of 80 rpm were set. Within a period of less than 30 min, a residual water content of less than 0.1% by weight was reached. The formic acid content was about 40% by weight.

Examples 18 to 21

Examples 18 to 21 were carried out in a similar manner to example 17. In each case a speed of rotation of 80 rpm was employed. The gas stream rate of nitrogen (example 18) or air (examples 19 to 21) was in each case 5 m³ (S.T.P.)/h, and drying was carried out in each case at atmospheric pressure. Further parameter values set as exceptions are indicated in each case in table 3 below. Table 3 also summarizes the results achieved in drying.

TABLE 3

| | Example No. | | | |
|---|---|---|---|---|
| | 18 | 19 | 20 | 21 |
| $T_{Gas}$ [°C.] | 54 | 52 | 60 | 50 |
| $T_{Wall}$ [°C.] | 26 | 26 | 26 | 40 |

TABLE 3-continued

| | Example No. | | | |
|---|---|---|---|---|
| | 18 | 19 | 20 | 21 |
| $T_{Prod}$ [°C.] | 28.6 | 30 | 36.7 | 39.5 |
| t [min] | 70 | 60 | 65 | 60 |
| $m_{Dry}$ [kg] | 2 | 1.97 | 2.2 | 2.2 |
| $H_2O_{Start}$ [% by weight] | 0.64 | 0.63 | 0.93 | 0.79 |
| $H_2O_{End}$ [% by weight] | 0.06 | 0.06 | 0.08 | 0.06 |
| $FA_{Start}$ [% by weight] | 41.52 | 41.23 | 42.05 | 41.52 |
| $FA_{End}$ [% by weight] | 40.31 | 40.16 | 40.51 | 40.34 |

$T_{Gas}$ = temperature of the inlet gas used for drying
$T_{Wall}$ = temperature of the dryer wall
$T_{Prod}$ = product temperature
t = total drying time
$m_{Dry}$ = total dry weight of the resultant product
$H_2O_{Start}$ = water content in the moist product at the start of drying
$H_2O_{End}$ = water content in the product at the end of drying
$FA_{Start}$ = formic acid content in the moist product at the start of drying
$FA_{End}$ = formic acid content in the product at the end of drying

The invention claimed is:

1. A sodium diformate in dry solid form comprising a formic acid content of at least 38% by weight, based on the total weight of sodium diformate.

2. The sodium diformate of claim 1 comprising a formic acid content in the range of from 38 to 41% by weight, based on the total weight of sodium diformate.

3. The sodium diformate of claim 1 comprising a water content not greater than 0.5% by weight, based on the total weight of sodium diformate.

4. The sodium diformate of claim 1, wherein said sodium diformate exhibits diffraction reflections in an x-ray powder diffractogram of at least at 6 of the following lattice separations d: 8.99; 7.40; 6.69; 5.12; 4.37; 3.83; 3.40; 3.10; 2.98; 2.94; 2.90 [Å] (±0.04 [Å]).

5. The sodium diformate of claim 1, wherein said sodium diformate has a phase transition point at a temperature of 65° C., as determined by means of differential scanning calorimetry.

* * * * *